(12) United States Patent
Fife et al.

(10) Patent No.: US 11,638,931 B2
(45) Date of Patent: May 2, 2023

(54) GETTER TECHNOLOGY FOR MICROMACHINED ULTRASONIC TRANSDUCER CAVITIES

(71) Applicant: BFLY OPERATIONS, INC., Guilford, CT (US)

(72) Inventors: Keith G. Fife, Palo Alto, CA (US); Lingyun Miao, Fremont, CA (US); Jianwei Liu, Fremont, CA (US); Jonathan M. Rothberg, Guilford, CT (US)

(73) Assignee: BFLY OPERATIONS, INC., Burlington, MA (US)

( * ) Notice: Subject to any disclaimer, the term of this patent is extended or adjusted under 35 U.S.C. 154(b) by 677 days.

(21) Appl. No.: 16/680,956

(22) Filed: Nov. 12, 2019

(65) Prior Publication Data

US 2020/0147641 A1   May 14, 2020

Related U.S. Application Data

(60) Provisional application No. 62/760,887, filed on Nov. 13, 2018.

(51) Int. Cl.
| | | |
|---|---|---|
| *B81B 7/00* | (2006.01) | |
| *B06B 1/02* | (2006.01) | |
| *B81C 1/00* | (2006.01) | |
| *A61B 8/00* | (2006.01) | |

(52) U.S. Cl.
CPC .......... *B06B 1/0292* (2013.01); *A61B 8/4494* (2013.01); *B81B 7/0038* (2013.01); *B81C 1/00285* (2013.01); *A61B 2562/12* (2013.01); *B06B 2201/76* (2013.01); *B81B 2201/0271* (2013.01); *B81B 2203/0127* (2013.01); *B81B 2203/0315* (2013.01); *B81B 2203/04* (2013.01)

(58) Field of Classification Search
CPC .............. B81B 7/0038; B81B 2203/04; B81B 2203/0315; B81B 2203/0127
See application file for complete search history.

(56) References Cited

U.S. PATENT DOCUMENTS

| | | |
|---|---|---|
| 8,222,065 B1 | 7/2012 | Smeys et al. |
| 9,067,779 B1 | 6/2015 | Rothberg et al. |
| 9,499,392 B2 | 11/2016 | Rothberg et al. |
| 9,533,873 B2 | 1/2017 | Rothberg et al. |
| 2009/0080292 A1 | 3/2009 | Wagner et al. |

(Continued)

FOREIGN PATENT DOCUMENTS

| | | |
|---|---|---|
| CN | 101394685 A | 3/2009 |
| CN | 104701452 A | 6/2015 |
| WO | WO 2020/069252 A1 | 4/2020 |

OTHER PUBLICATIONS

Invitation to Pay Additional Fees dated Jan. 15, 2020 in connection with International Application No. PCT/US2019/060826.

(Continued)

*Primary Examiner* — Samuel A Gebremariam
(74) *Attorney, Agent, or Firm* — Osha Bergman Watanabe & Burton LLP (57) ABSTRACT

A method of forming an ultrasonic transducer device includes bonding a membrane to seal a transducer cavity with at least a portion of a getter material layer being exposed, the getter material layer comprising a portion of a bilayer stack compatible for use in damascene processing.

15 Claims, 8 Drawing Sheets

(56) References Cited

U.S. PATENT DOCUMENTS

| | | |
|---|---|---|
| 2010/0323469 A1 | 12/2010 | Borthakur et al. |
| 2011/0055447 A1 | 3/2011 | Costa |
| 2013/0171797 A1* | 7/2013 | Park .................. H01L 21/02194 |
| | | 257/E21.409 |
| 2016/0009544 A1 | 1/2016 | Rothberg et al. |
| 2016/0101976 A1 | 4/2016 | Hsieh et al. |
| 2016/0280538 A1 | 9/2016 | Rothberg et al. |
| 2016/0362295 A1 | 12/2016 | Quevy et al. |
| 2017/0143306 A1 | 5/2017 | Rothberg et al. |
| 2019/0160490 A1 | 5/2019 | Alie et al. |
| 2019/0231312 A1 | 8/2019 | Fife et al. |
| 2019/0275561 A1 | 9/2019 | Fife et al. |
| 2019/0336099 A1 | 11/2019 | Fife et al. |
| 2019/0336103 A1 | 11/2019 | Fife et al. |
| 2019/0336104 A1 | 11/2019 | Fife et al. |
| 2020/0013691 A1 | 1/2020 | Liu et al. |
| 2020/0102214 A1 | 4/2020 | Liu et al. |

OTHER PUBLICATIONS

International Search Report and Written Opinion dated Mar. 9, 2020 in connection with International Application No. PCT/US2019/060826.

International Preliminary Report on Patentability dated May 27, 2021 in connection with International Application No. PCT/US2019/060826.

Extended European Search Report dated Jun. 21, 2022 in connection with European Application No. 19885512.

PCT/US2019/060826, Jan. 15, 2020, Invitation to Pay Additional Fees.

PCT/US2019/060826, Mar. 9, 2020, International Search Report and Written Opinion.

* cited by examiner

GETTER TECHNOLOGY FOR MICROMACHINED ULTRASONIC TRANSDUCER CAVITIES

CROSS-REFERENCE TO RELATED APPLICATIONS

The present application claims the benefit under 35 U.S.C. § 119(e) of U.S. Provisional Patent Application Ser. No. 62/760,887, filed Nov. 13, 2018, and entitled "THIN FILM CAVITY GETTER MATERIAL FOR MICROMACHINED ULTRASONIC TRANSDUCER DEVICES," which is hereby incorporated herein by reference in its entirety.

BACKGROUND

The present disclosure relates generally to micromachined ultrasonic transducers and, more specifically, to a thin film getter material for use in micromachined ultrasonic transducer cavities and transducer manufacturing techniques.

Ultrasound devices may be used to perform diagnostic imaging and/or treatment, using sound waves with frequencies that are higher than those audible to humans. When pulses of ultrasound are transmitted into tissue, sound waves are reflected off the tissue with different tissues reflecting varying degrees of sound. These reflected sound waves may then be recorded and displayed as an ultrasound image to the operator. The strength (amplitude) of the sound signal and the time it takes for the wave to travel through the body provide information used to produce the ultrasound images.

Some ultrasound imaging devices may be fabricated using micromachined ultrasonic transducers, including a flexible membrane suspended above a substrate. A cavity is located between part of the substrate and the membrane, such that the combination of the substrate, cavity and membrane form a variable capacitor. When actuated by an appropriate electrical signal, the membrane generates an ultrasound signal by vibration. In response to receiving an ultrasound signal, the membrane is caused to vibrate and, as a result, generates an output electrical signal.

SUMMARY

In one aspect, a method of forming an ultrasonic transducer device includes bonding a membrane to seal a transducer cavity with at least a portion of a getter material layer being exposed, the getter material layer comprising a portion of a bilayer stack compatible for use in damascene processing.

In another aspect, a method of forming an ultrasonic transducer device includes forming a diffusion barrier layer over a substrate; forming a getter material layer over the diffusion barrier layer; forming a metal electrode layer over a first portion of the getter material layer; forming a transducer cavity over the metal electrode layer; and bonding a membrane to seal the transducer cavity with at least a second portion of the getter material layer being exposed.

In another aspect, a method of forming an ultrasonic transducer device includes forming a bilayer stack over a substrate having a first metal layer therein, the bilayer stack comprising a diffusion barrier layer and a getter material layer formed on the diffusion barrier layer; patterning the bilayer stack; forming a first dielectric layer over the patterned bilayer stack; patterning the first dielectric layer so as to expose first portions of the patterned bilayer stack and a portion of the first metal layer, with second portions of the patterned bilayer stack being protected by the patterned first dielectric layer; forming a second metal layer over the first portions of the patterned bilayer stack, the portion of the first metal layer and the patterned first dielectric layer, and planarizing the second metal layer and patterned first dielectric layer; forming a bottom capping layer over the planarized second metal layer and patterned first dielectric layer, and forming a transducer cavity sidewall layer over the bottom capping layer; patterning the transducer cavity sidewall layer to define a transducer cavity; removing a portion of the bottom capping layer and second portions of the patterned first dielectric layer to expose the getter material layer; and bonding a membrane to seal the transducer cavity.

In another aspect, an ultrasonic transducer device includes a substrate having a first metal layer formed therein, the bilayer stack comprising a diffusion barrier layer and a getter material layer formed on the diffusion barrier layer; a patterned bilayer stack formed above the first metal layer; a second metal layer formed on a first portion of the bilayer stack; a bottom capping layer formed over the second metal layer; and a transducer cavity defined over the bottom capping layer and a membrane that seals the transducer cavity; wherein a portion of the bottom cavity layer has an opening formed therein so as to expose the getter material layer corresponding to a second portion of the bilayer stack.

BRIEF DESCRIPTION OF THE DRAWINGS

Various aspects and embodiments of the application will be described with reference to the following figures. It should be appreciated that the figures are not necessarily drawn to scale. Items appearing in multiple figures are indicated by the same reference number in all the figures in which they appear.

FIGS. 2-1 through 2-10 are a series of cross-sectional views illustrating an exemplary process flow for forming a micromachined ultrasonic transducer device having a thin film getter material according to an embodiment.

DETAILED DESCRIPTION

The techniques described herein relate to fabrication of a thin film getter material for micromachined ultrasonic transducer cavities.

One type of transducer suitable for use in ultrasound imaging devices is a micromachined ultrasonic transducer (MUT), which can be fabricated from, for example, silicon and configured to transmit and receive ultrasound energy. MUTs may include capacitive micromachined ultrasonic transducers (CMUTs) and piezoelectric micromachined ultrasonic transducers (PMUTs), both of which can offer several advantages over more conventional transducer designs such as, for example, lower manufacturing costs and fabrication times and/or increased frequency bandwidth. With respect to the CMUT device, the basic structure is a parallel plate capacitor with a rigid bottom electrode and a top electrode residing on or within a flexible membrane. Thus, a cavity is defined between the bottom and top electrodes. In some designs (such as those produced by the assignee of the present application for example), a CMUT may be directly integrated on an integrated circuit that controls the operation of the transducer. One way of manufacturing a CMUT is to bond a membrane substrate to an integrated circuit substrate, such as a complementary metal oxide semiconductor (CMOS) substrate. This may be performed at temperatures sufficiently low to prevent damage to the devices of the integrated circuit.

Figure 1A:
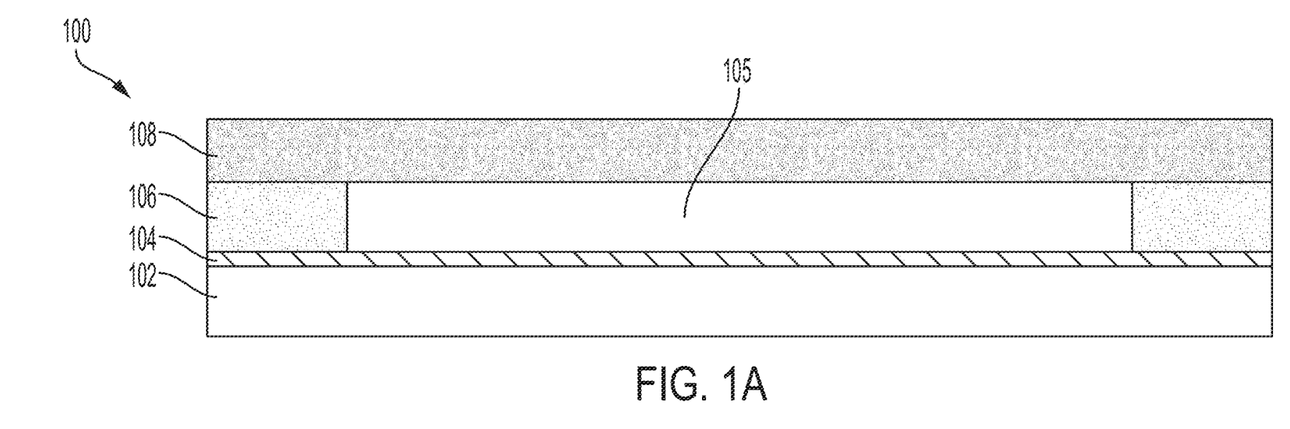
FIG. 1A is a cross-sectional view of an exemplary micromachined ultrasonic transducer device.

Referring initially now to FIG. 1A, there is shown a cross-sectional view of an exemplary micromachined ultrasonic transducer device 100, such as a CMUT. The transducer device 100 includes a substrate, generally designated by 102, (e.g., a complementary metal oxide semiconductor (CMOS) substrate, such as silicon) having one or more layers such as for example: CMOS circuits, wiring layers, redistribution layers, insulation/passivation layers and one or more metal electrode layers that may serve as a transducer bottom electrode. The substrate 102 (including transducer bottom electrode) may have one or more insulating layers formed thereon, generally designated by layer 104. A transducer cavity 105 is defined by lithographic patterning and etching of a support layer 106 that is formed on stack 104. The support layer 106 may be an insulating layer, such as $SiO_2$ for example, the remaining portions of which provide a support surface to which a transducer membrane 108 is bonded.

Figure 1B:
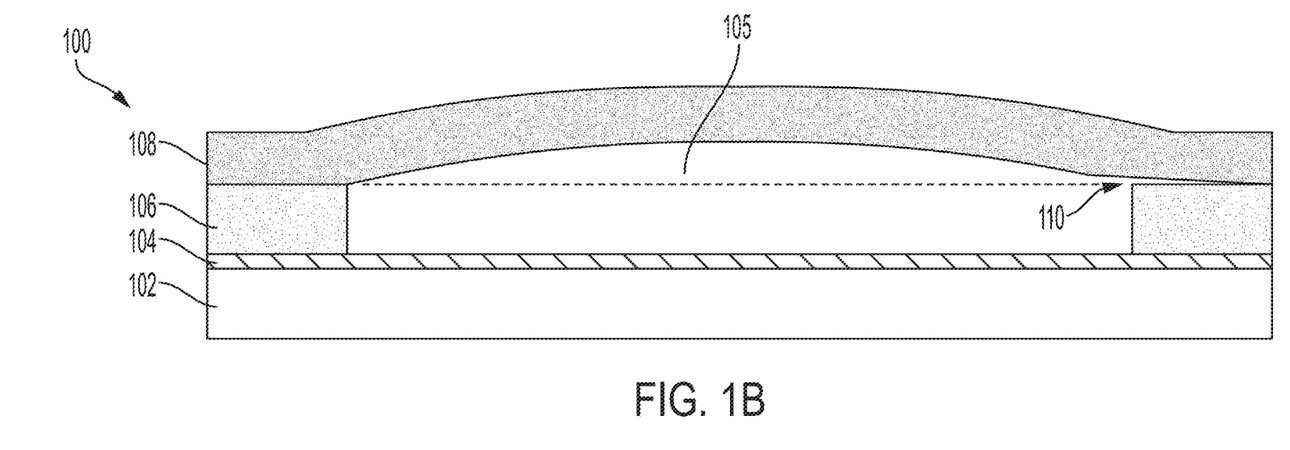
FIG. 1B is a cross-sectional view of an exemplary micromachined ultrasonic transducer device having a delamination defect due to high cavity pressure during membrane bonding.

During bonding of the transducer membrane 108 to the support layer 106, the structure may be subject to relatively high pressures and/or exposed to one or more bonding byproducts such as, for example, nitrogen, oxygen and water vapor. As a result, one possible side effect of such processing is illustrated in FIG. 1B. As shown, high cavity pressures (e.g., on the order of about 10 atm or more) may result in delamination (indicated by arrow 110) of the membrane 108 from the support layer 106.

Figure 1C:
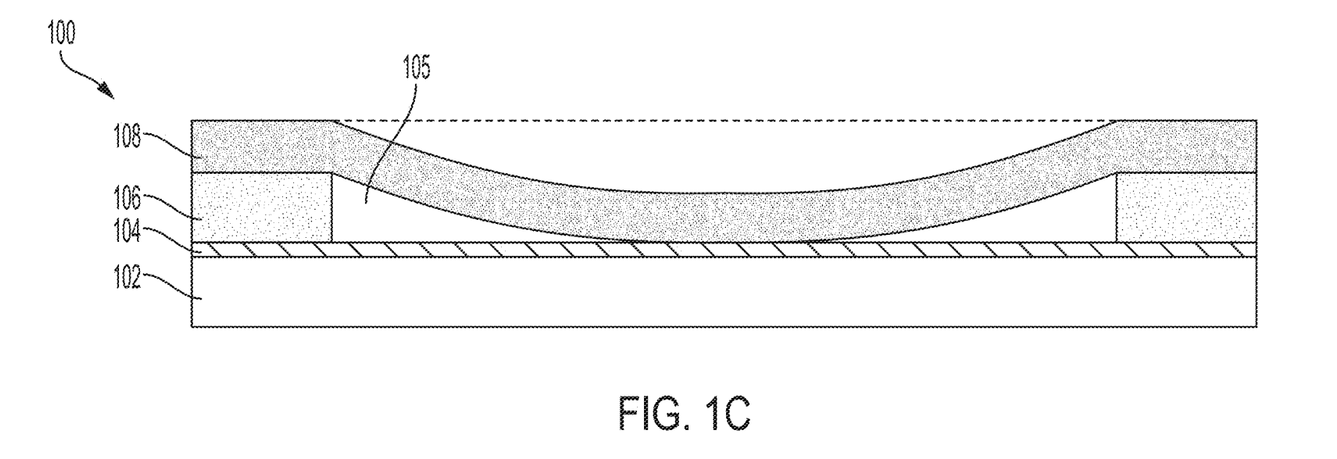
FIG. 1C is a cross-sectional view of an exemplary micromachined ultrasonic transducer device having a stuck cell defect due to stiction effects.

In addition, during operation of the transducer device 100, whether in a transmit mode and/or a receive mode, the transducer membrane 108 may come into physical contact with the top of the stack 104 (i.e., the bottom surface of the cavity 105), as depicted in FIG. 1C. This position may be indicative of the so-called "collapse mode" of operation as known in the art. A "collapse mode" (also used interchangeably with the term "collapsed mode") refers to a mode of transducer operation in which at least one portion of a micromachined ultrasonic transducer membrane is mechanically fixed and at least one portion of the membrane is free to vibrate based on a changing voltage differential between the electrode and the membrane. On one hand, operating a micromachined ultrasonic transducer in collapse mode may optimize the acoustic power (output pressure) produced by the transducer. On the other hand, however, one side effect of a micromachined ultrasonic transducer operating in collapse mode may be charge retention (also known as "charge trapping"), wherein the membrane and/or the bottom cavity surface undesirably stores charge or conducts leakage current. As a result, this charge retention may in turn undesirably alter an applied voltage at which membrane collapse is induced during device operation. Another possible side effect of collapse mode for the transducer 100 shown in FIG. 1C may be stiction, which is associated with the amount of surface area of contact between the membrane 108 and the bottom surface of the cavity 105 wherein the two surfaces inadvertently stick to one another due to excess moisture present in the cavity 105 during membrane bonding.

Figure 3:
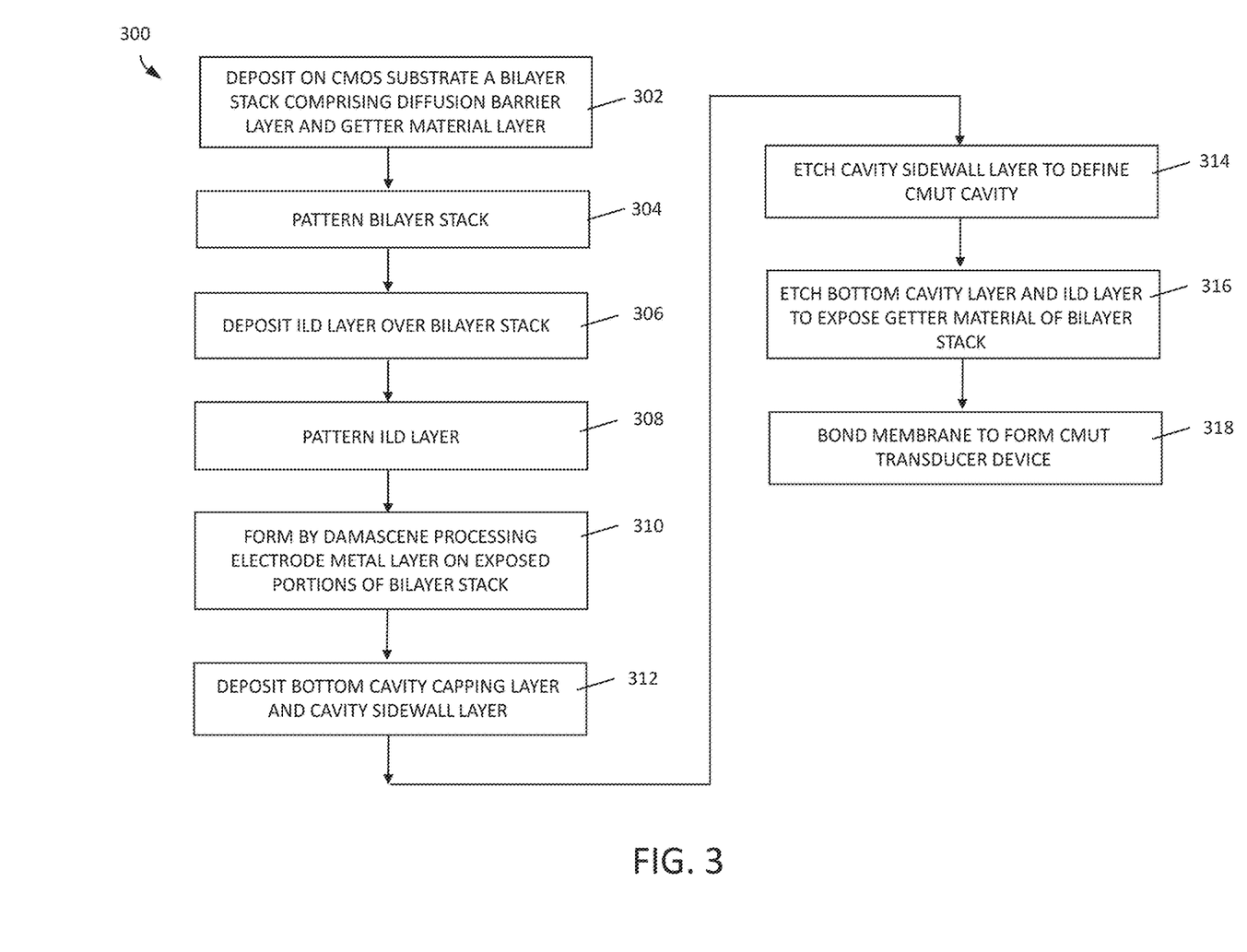
FIG. 3 is a flow diagram describing the exemplary process flow of FIGS. 2-1 through 2-10.

Accordingly, FIGS. 2-1 through 2-10 are a series of cross-sectional views illustrating an exemplary process flow for forming a micromachined ultrasonic transducer device having a thin film getter material according to an embodiment. In addition, FIG. 3 is a flow diagram 300 describing the exemplary process flow of FIGS. 2-1 through 2-10. As will be illustrated in further detail below, not only does the thin film metal serve as a getter for absorbing certain cavity gas species to maintain cavity pressure to a desired level, the exemplary process flow is also capable of smoothly integrating with high-throughput metal (e.g., copper) damascene processing techniques.

Figure 21:
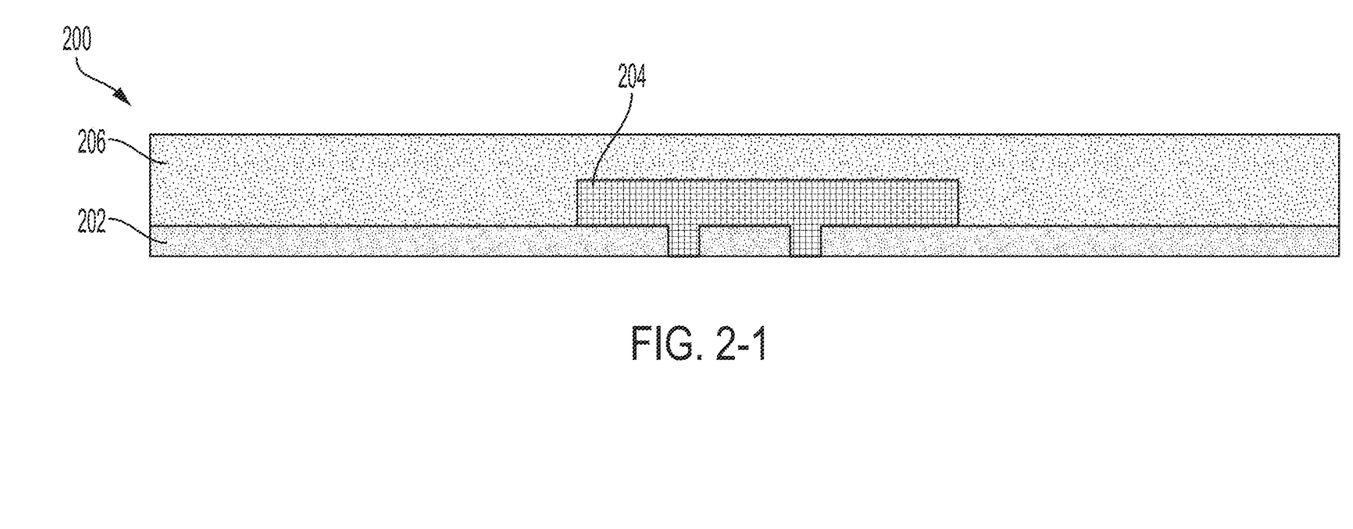

FIG. 2-1 illustrates a CMOS substrate 200, e.g., a complementary metal oxide semiconductor (CMOS) substrate, such as silicon, having one or more layers (generally designated by 202) such as for example: CMOS circuits, wiring layers, redistribution layers and insulation/passivation layers. A metal layer 204 (e.g., copper) having a thickness of about 1-2 microns (μm) is formed on the layer(s) 202, with an interlevel dielectric (ILD) layer 206 (e.g., $SiO_2$) formed over the metal layer 204 and layer(s) 202. The ILD layer 206 may have a thickness of about 1-2 μm. It should be appreciated that the various layers depicted in FIG. 2-1 are not necessarily shown to scale, and in particular the layer(s) 202 of CMOS substrate 200 may be thicker than the layers subsequently formed thereon.

Figure 22:
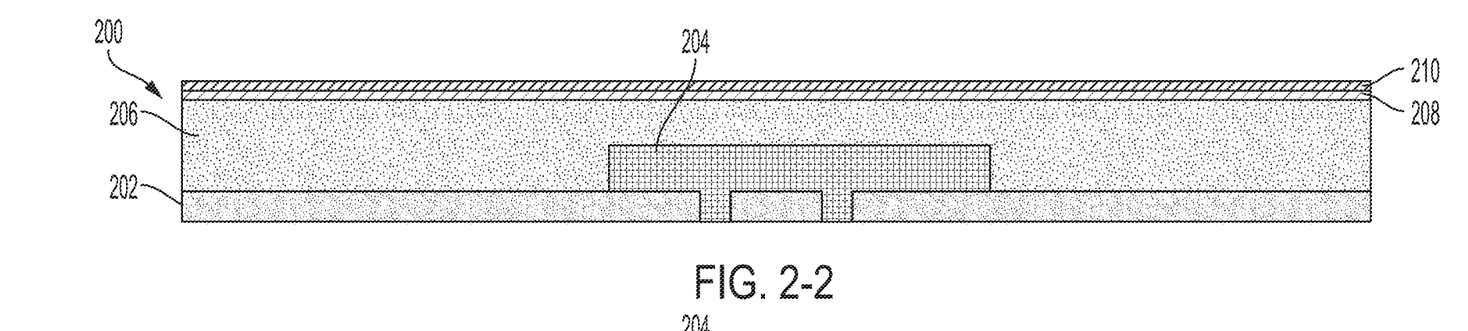

As shown in FIG. 2-2 and indicated in block 302 of FIG. 3, a bilayer stack comprising a diffusion barrier layer 208 and getter material layer 210 is deposited on the structure of FIG. 2-1. In an embodiment, the diffusion barrier layer 208 may be formed from a material such as tantalum nitride (TaN) having a thickness of about 8-12 nanometers (nm), which is effective to resist copper diffusion during subsequent device processing. The getter material layer 210 may be a thicker layer of getter material, such as Ta or Ti for example, formed at a thickness of about 50-100 nm. Where Ta is the getter material of choice, processing operations may be simplified in that the same chamber may be used to complete the bilayer stack deposition (e.g., TaN deposition, followed by shutting off nitrogen into the deposition chamber to form Ta getter material).

Figure 23:
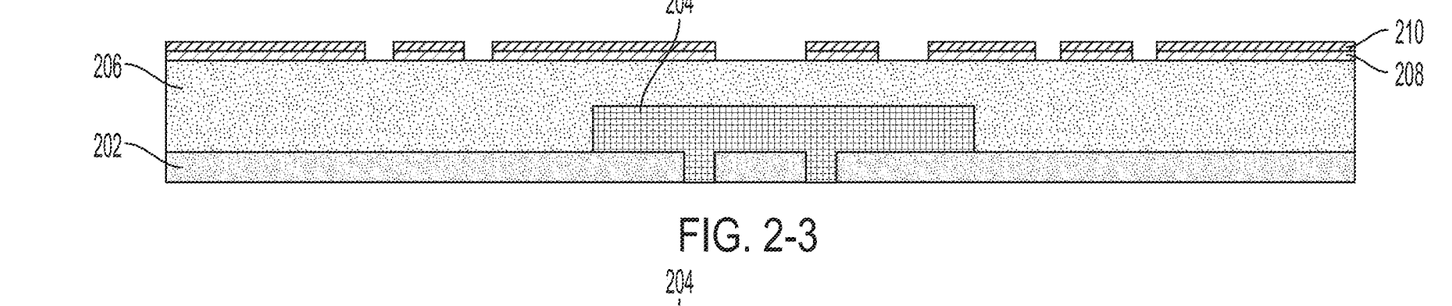
Figure 24:
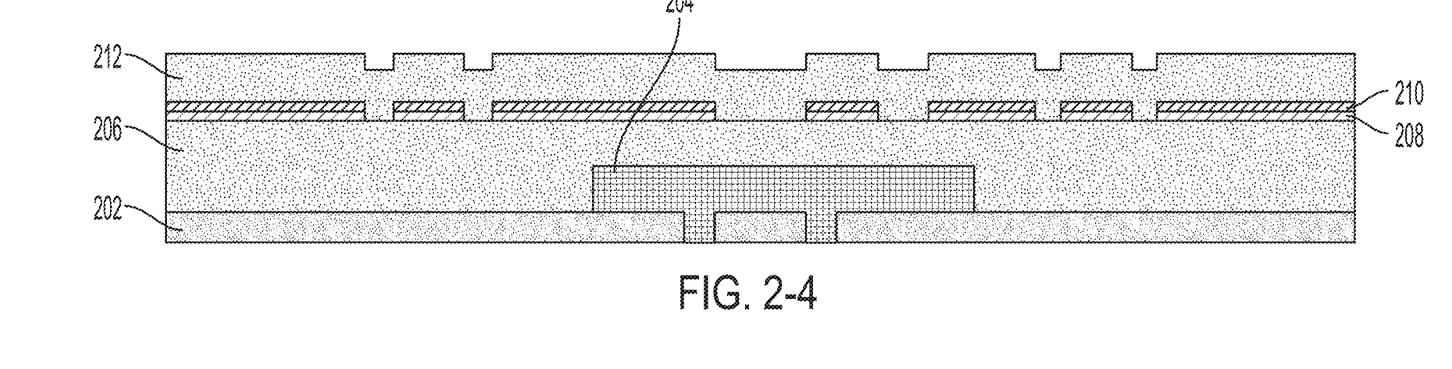

Referring to FIG. 2-3 and block 304 of FIG. 3, the bilayer stack 208/210 is patterned (e.g., by photolithography and etching). The resulting pattern of bilayer stack material may correspond to desired locations of a transducer bottom electrode material and transducer cavity getter material. Following the patterning of the bilayer stack 208/210, an ILD layer 212 is formed over the resulting structure, as shown in FIG. 2-4 and indicated in block 306 of FIG. 3. The ILD layer 212 may be, for example, $SiO_2$ formed at a thickness of about 300-800 nm, and may be a conformal layer with a resulting topography that corresponds to the topography of the patterned bilayer stack 208/210.

Figure 25:
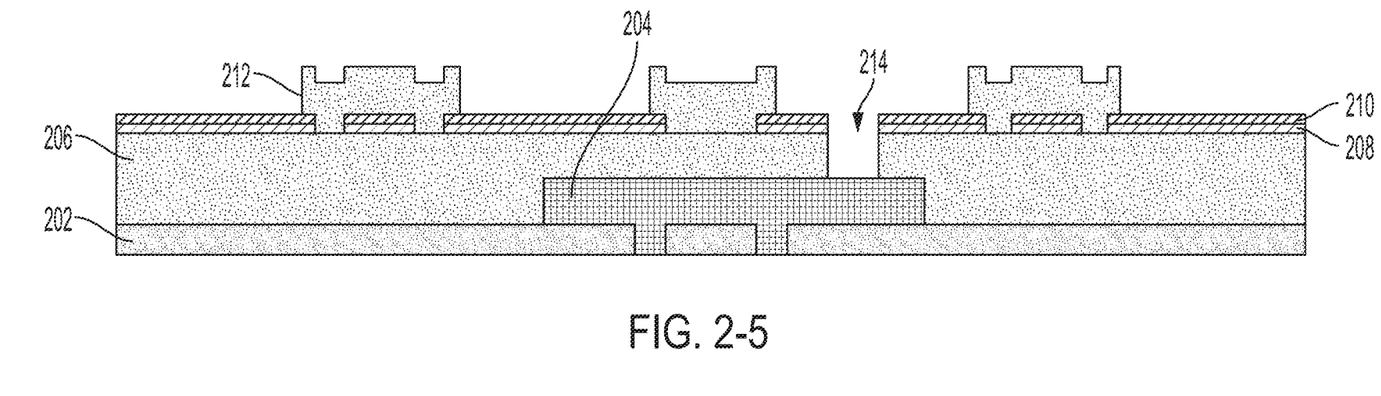
Figure 26:
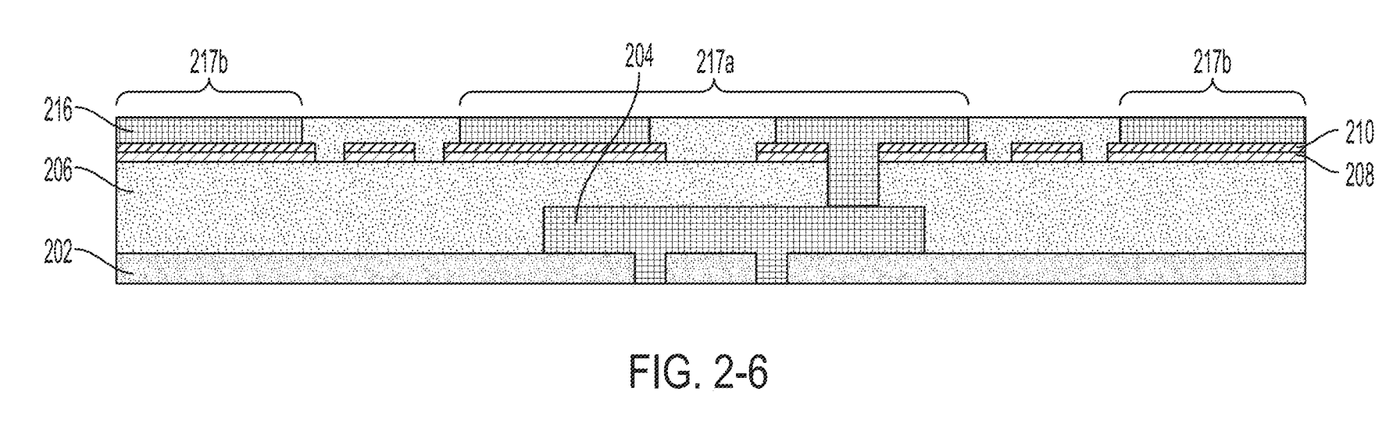

As then shown in FIG. 2-5 and indicated in block 308 of FIG. 3, the ILD layer 212 is patterned (e.g., by photolithography and etching) with the bilayer stack 208/210 serving as an etch stop. The patterning of ILD layer 212 may also define a via 214 that exposes a portion of the metal layer 204. Following patterning of the ILD layer, a damascene metal plating operation is implemented over the structure, followed by planarization of the excess metal as indicated in block 310 of FIG. 3 to form the structure shown in FIG. 2-6. Plating may include forming a seed layer (not shown) and a metal layer 216 (e.g., copper) initially formed to a thickness of about 1.5-2.5 μm thick. A chemical mechanical polishing (CMP) operation is then performed to polish the excess copper back and smooth out the existing surface topography as shown in FIG. 2-6. The remaining metal layer 216 after CMP may have a thickness of about 200-300 nm and, as also shown in FIG. 2-6, fills the via 214 that was formed in FIG. 2-5 so as to make electrical contact with the metal layer 204. In the embodiment depicted, the region 217a of metal layer 216 that contacts metal layer 204 corresponds to a transducer bottom electrode (e.g., a donut shaped electrode), while the regions 217b of metal layer 216 may correspond to bypass metal for the transducer. However, it should be appreciated that since specific transducer bottom electrode patterns are not the focus of the present disclosure, it is contemplated that the present embodiments may also be implemented in conjunction with several other transducer electrode patterns and designs including (but not limited to), multiple segment or ring electrodes, and additional metal patterns used for other purposes besides bottom electrodes.

Figure 27:
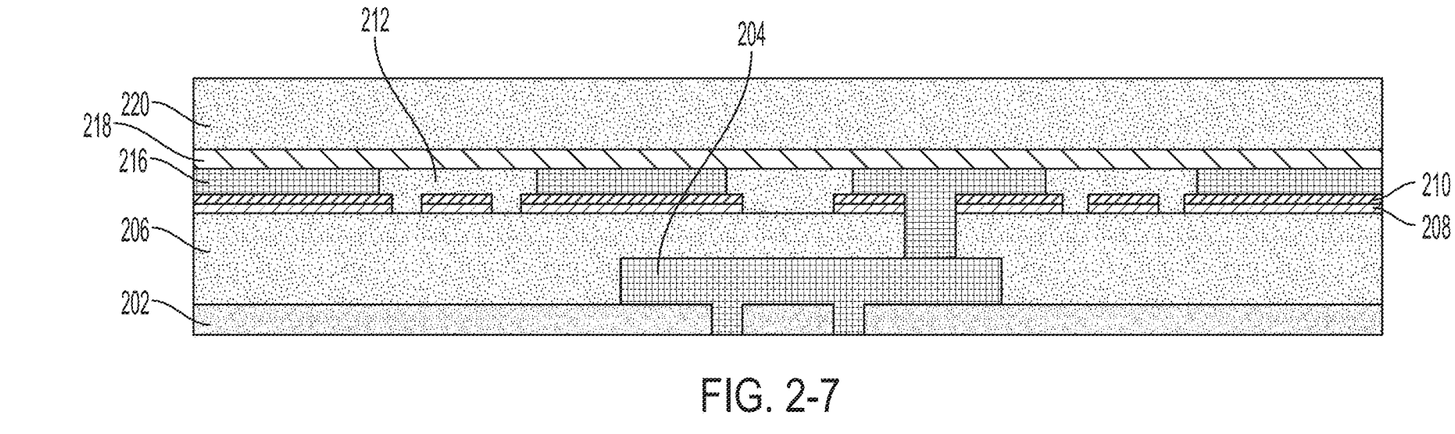
Figure 28:
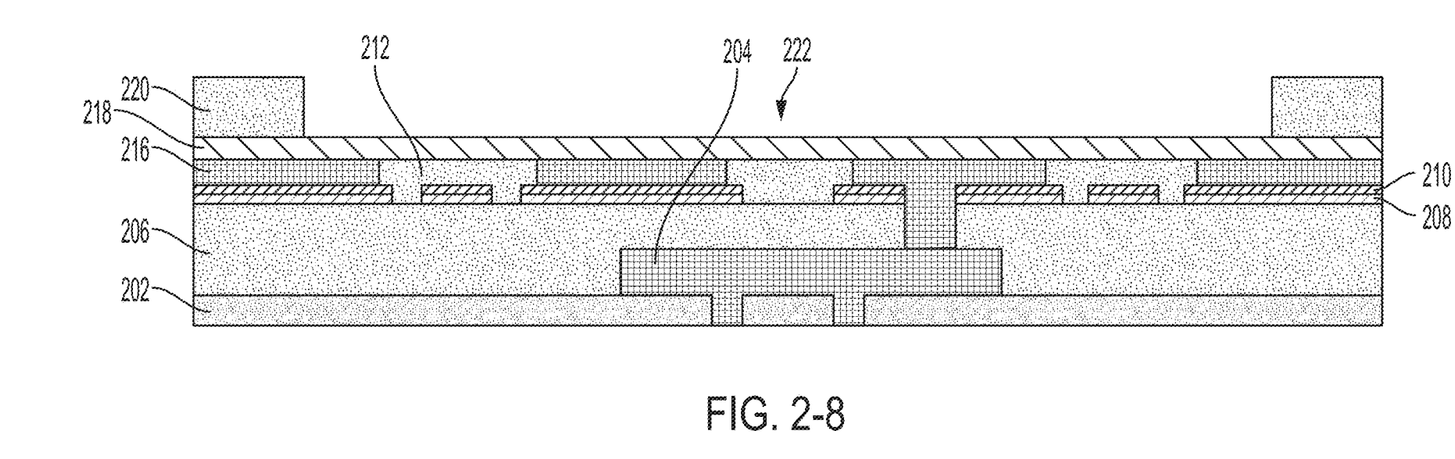

Proceeding to FIG. 2-7, the process continues with the formation of a bottom cavity capping layer 218 and transducer cavity sidewall layer 220 as indicated in block 312 of FIG. 3. The bottom cavity capping layer 218 may be a thin film layer such as aluminum oxide ($Al_2O_3$) formed by atomic layer deposition (ALD) at a thickness of about 20-30 nm, and the transducer cavity sidewall layer 220 may be $SiO_2$ formed at a thickness of about 200-300 nm. A transducer cavity 222 is then formed by patterning the transducer cavity sidewall layer 220 as illustrated in FIG. 2-8 and indicated in block 314 of FIG. 3.

Figure 29:
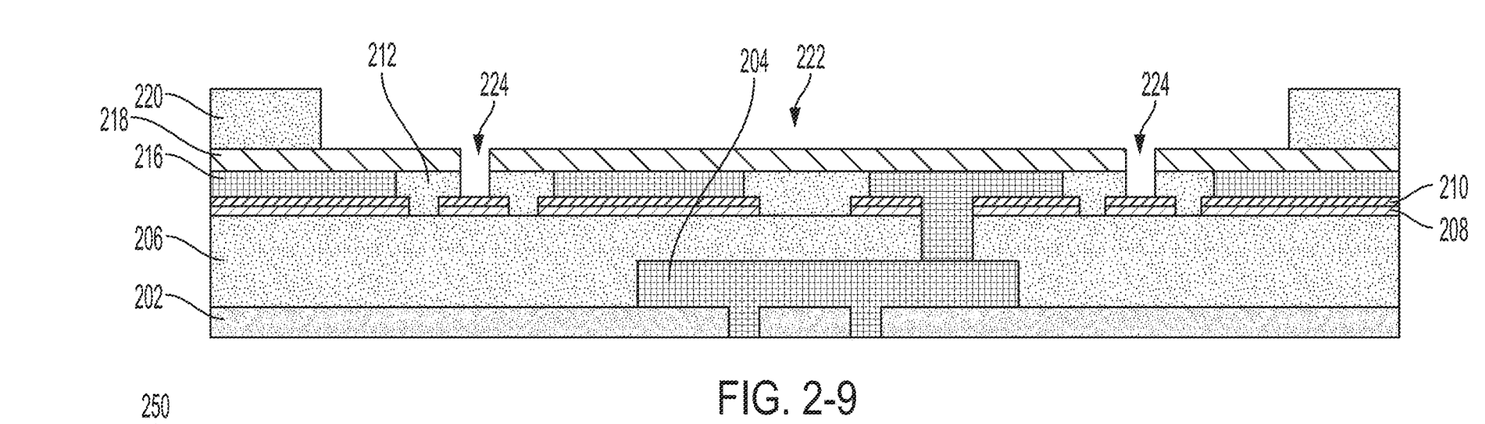
Figure 210:
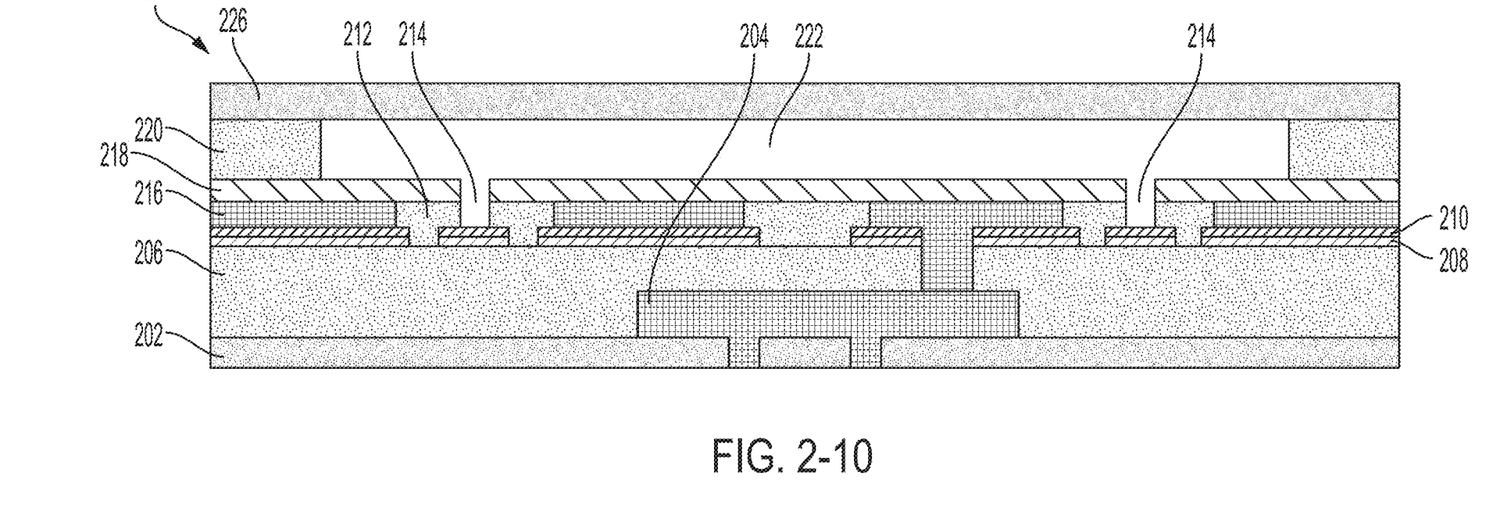

Once the cavity etch is complete, another etch is performed to form openings 224 through the bottom cavity capping layer 218 and ILD layer 214 so as to expose portions of the getter material layer 210, as illustrated in FIG. 2-9 and depicted in block 316 of FIG. 3. Notably, the exposed portions of the getter material layer 210 correspond to particular locations of the bilayer stack 208/210 that are not used for plating the metal layer 216 (i.e., locations protected by remaining ILD layer 210). Accordingly, when a membrane layer 226 is bonded to the transducer cavity sidewall layer 220 to seal the cavity 222 and define an ultrasonic transducer 250, as shown in FIG. 2-10 and indicated in block 318 of FIG. 3, the exposed getter material layer 210 may absorb certain cavity gas species and help maintain cavity pressure at a desired level. Moreover, by incorporating the getter material with the diffusion barrier layer 208 as part of a bilayer stack, the gettering process scheme is advantageously incorporated with high-throughput damascene processing techniques. From this point, additional processing as known in the art may continue to complete fabrication of an ultrasonic transducer device. It should further be appreciated that although the illustrated embodiments depict a single cavity for ease of illustration, any suitable number of cavities and corresponding electrode structures may be formed (e.g., hundreds, thousands, tens of thousands, etc.)

Figure 4:
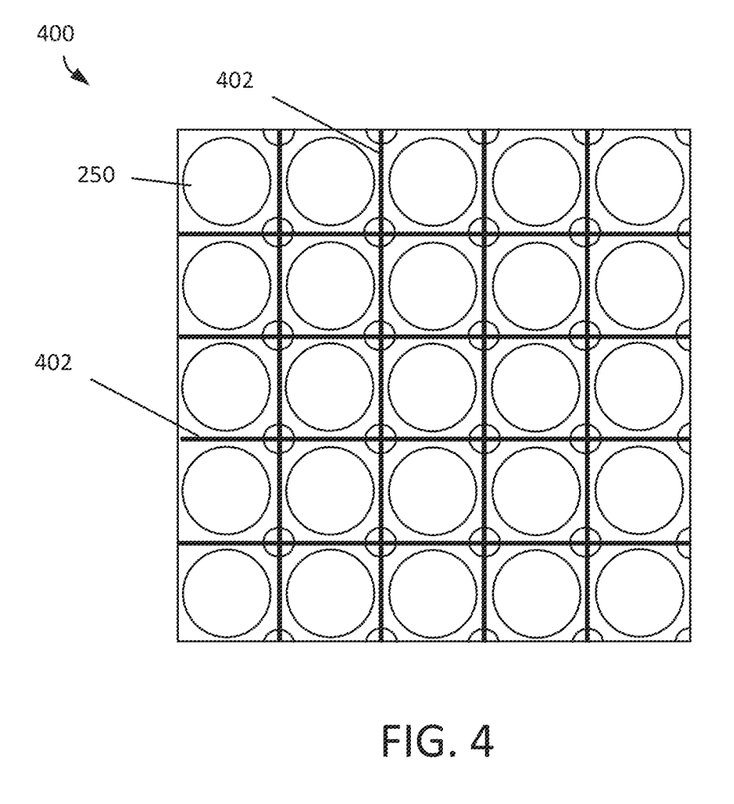
FIG. 4 is a top view of an example ultrasonic transducer device formed using the process flow of FIGS. 2-1 through 2-10 and FIG. 3.

FIG. 4 illustrates a top view of an example ultrasonic transducer device 400 that may be formed using the exemplary process flow embodiments described herein. As illustrated, the transducer device 400 includes an array of individual transducers 250, such as those described above. The specific number of transducers 250 shown in FIG. 4 should not be construed in any limiting sense, and may include any number suitable for a desired imaging application, which may be for example on the order of tens, hundreds, thousands, tens of thousands or more. FIG. 4 further illustrates an example location of metal 402 that may distribute an electrical signal to the membranes (upper electrodes) of the transducers 250.

It should be further appreciated that although the exemplary geometric structure of this portion of the ultrasonic transducer 250 is generally circular in shape, other configurations are also contemplated such as for example, rectangular, hexagonal, octagonal, and other multi-sides shapes, etc.

The above-described embodiments can be implemented in any of numerous ways. For example, the embodiments may be implemented using hardware, software or a combination thereof. When implemented in software, the software code can be executed on any suitable processor (e.g., a microprocessor) or collection of processors, whether provided in a single computing device or distributed among multiple computing devices. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, some aspects of the technology may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

What is claimed is:

1. A method of forming an ultrasonic transducer device, the method comprising:
   patterning a bilayer stack compatible for use in damascene processing and forming a metal layer on a first portion of the bilayer stack; and
   bonding a membrane to seal a transducer cavity with at least a portion of a getter material layer being exposed, the getter material layer corresponding to a second portion of the bilayer stack without the metal layer formed thereon.

2. The method of claim 1, wherein the bilayer stack comprises a diffusion barrier layer and the getter material layer formed on the diffusion barrier layer.

3. The method of claim 2, wherein the diffusion barrier layer comprises tantalum nitride (TaN), and the getter material layer comprises one of: tantalum (Ta) or titanium (Ti).

4. The method of claim 1, further comprising exposing the exposed portion of the getter material layer by forming an opening through a bottom capping layer and a dielectric layer disposed over the second portion of the bilayer stack.

5. A method of forming an ultrasonic transducer device, the method comprising:
   forming a diffusion barrier layer over a substrate;
   forming a getter material layer over the diffusion barrier layer;
   forming a metal electrode layer over a first portion of the getter material layer;
   forming a transducer cavity over the metal electrode layer; and
   bonding a membrane to seal the transducer cavity with at least a second portion of the getter material layer being exposed.

6. The method of claim 5, wherein the diffusion barrier layer comprises tantalum nitride (TaN), and the getter material layer comprises one of: tantalum (Ta) or titanium (Ti).

7. The method of claim 5, further comprising:
   patterning the getter material layer and the diffusion barrier layer;
   forming a dielectric layer over the getter material layer and diffusion barrier layer;
   patterning the dielectric layer to expose the first portion of the getter material layer; and
   forming the metal electrode layer over the first portion of the getter material layer.

8. The method of claim 7, wherein forming the metal electrode layer further comprises:
   plating the metal electrode layer over the first portion of the getter material layer and the patterned dielectric layer; and
   planarizing the plated metal electrode layer and patterned dielectric layer such that the metal electrode layer covers the first portion of the getter material layer and the patterned dielectric layer covers the second portion of the getter material layer.

9. The method of claim 8, further comprising:
   forming a bottom capping layer over the planarized metal electrode layer and patterned dielectric layer;
   forming a transducer cavity sidewall layer over the bottom capping layer;
   patterning the transducer cavity sidewall layer to define the transducer cavity; and
   removing a portion of the bottom capping layer and portions of the patterned dielectric layer to expose the second portion of the getter material layer.

10. A method of forming an ultrasonic transducer device, the method comprising:
    forming a bilayer stack over a substrate having a first metal layer therein, the bilayer stack comprising a diffusion barrier layer and a getter material layer formed on the diffusion barrier layer;
    patterning the bilayer stack;
    forming a first dielectric layer over the patterned bilayer stack;
    patterning the first dielectric layer so as to expose first portions of the patterned bilayer stack and a portion of the first metal layer, with second portions of the patterned bilayer stack being protected by the patterned first dielectric layer;
    forming a second metal layer over the first portions of the patterned bilayer stack, the portion of the first metal layer and the patterned first dielectric layer, and planarizing the second metal layer and patterned first dielectric layer;
    forming a bottom capping layer over the planarized second metal layer and patterned first dielectric layer, and forming a transducer cavity sidewall layer over the bottom capping layer;
    patterning the transducer cavity sidewall layer to define a transducer cavity;
    removing a portion of the bottom capping layer and second portions of the patterned first dielectric layer to expose the getter material layer; and
    bonding a membrane to seal the transducer cavity.

11. The method of claim 10, wherein the bilayer stack comprises a diffusion barrier layer and the getter material layer formed on the diffusion barrier layer.

12. The method of claim 11, wherein the diffusion barrier layer comprises tantalum nitride (TaN), and the getter material layer comprises one of: tantalum (Ta) or titanium (Ti).

13. The method of claim 11, wherein the diffusion barrier layer is formed at a thickness of about 8-10 nanometers (nm), and the getter material layer at a thickness of about 50-100 nm.

14. The method of claim 10, wherein the bottom capping layer comprises aluminum oxide ($Al_2O_3$) formed by atomic layer deposition (ALD).

15. The method of claim 14, wherein the bottom capping layer is formed at thickness of about 20-30 nm.

* * * * *